United States Patent [19]

Li

[11] 4,023,216
[45] May 17, 1977

[54] URINAL DEVICE

[75] Inventor: Laurie Rhea Li, Downey, Calif.

[73] Assignee: Victor F. C. Li, Downey, Calif.

[22] Filed: Apr. 30, 1975

[21] Appl. No.: 573,249

Related U.S. Application Data

[63] Continuation-in-part of Ser. No. 527,887, Nov. 27, 1974, abandoned.

[52] U.S. Cl. ..................................... 4/110; 4/112; 128/295
[51] Int. Cl.² ......................................... E03D 13/00
[58] Field of Search ............... 4/110, 114, 111, 99, 4/112, 113, 142, 138; 128/295; 229/22

[56] References Cited

UNITED STATES PATENTS

| | | | |
|---|---|---|---|
| 190,244 | 5/1877 | Olmstead | 4/110 |
| 2,685,399 | 8/1954 | Crosby | 229/22 |
| 2,968,046 | 1/1961 | Duke | 128/295 X |
| 3,099,017 | 7/1963 | Sullivan | 4/110 |
| 3,335,714 | 8/1967 | Giesy | 4/110 X |
| 3,511,241 | 5/1970 | Lee | 128/295 |
| 3,535,714 | 10/1970 | Bjork | 4/110 X |
| 3,613,122 | 10/1971 | Gross et al. | 4/110 |
| 3,731,869 | 5/1973 | Griffin | 229/22 |
| 3,742,523 | 7/1973 | Atkins | 4/110 |

*Primary Examiner*—Henry K. Artis
*Attorney, Agent, or Firm*—J. C. Baisch

[57] ABSTRACT

A rigid device of plastic or other suitable material which will gather the poorly defined urinary efflux of a urinating human female in a normal standing position and direct it forwardly and downwardly in a defined stream to impinge on a chosen spot. The device comprises a trough open at the top and adapted to be positioned to register with outlet of the urethra. From the forward end of the trough, there is a forwardly and downwardly inclined discharge conduit and there is also an absorbent pad at the rear of the trough to remove residual urine from the internal and external vulvae which comprises material that has a blotting action. This material is replaceable. Another embodiment is of foldable material such as suitable paper with a waterproof lining.

8 Claims, 8 Drawing Figures

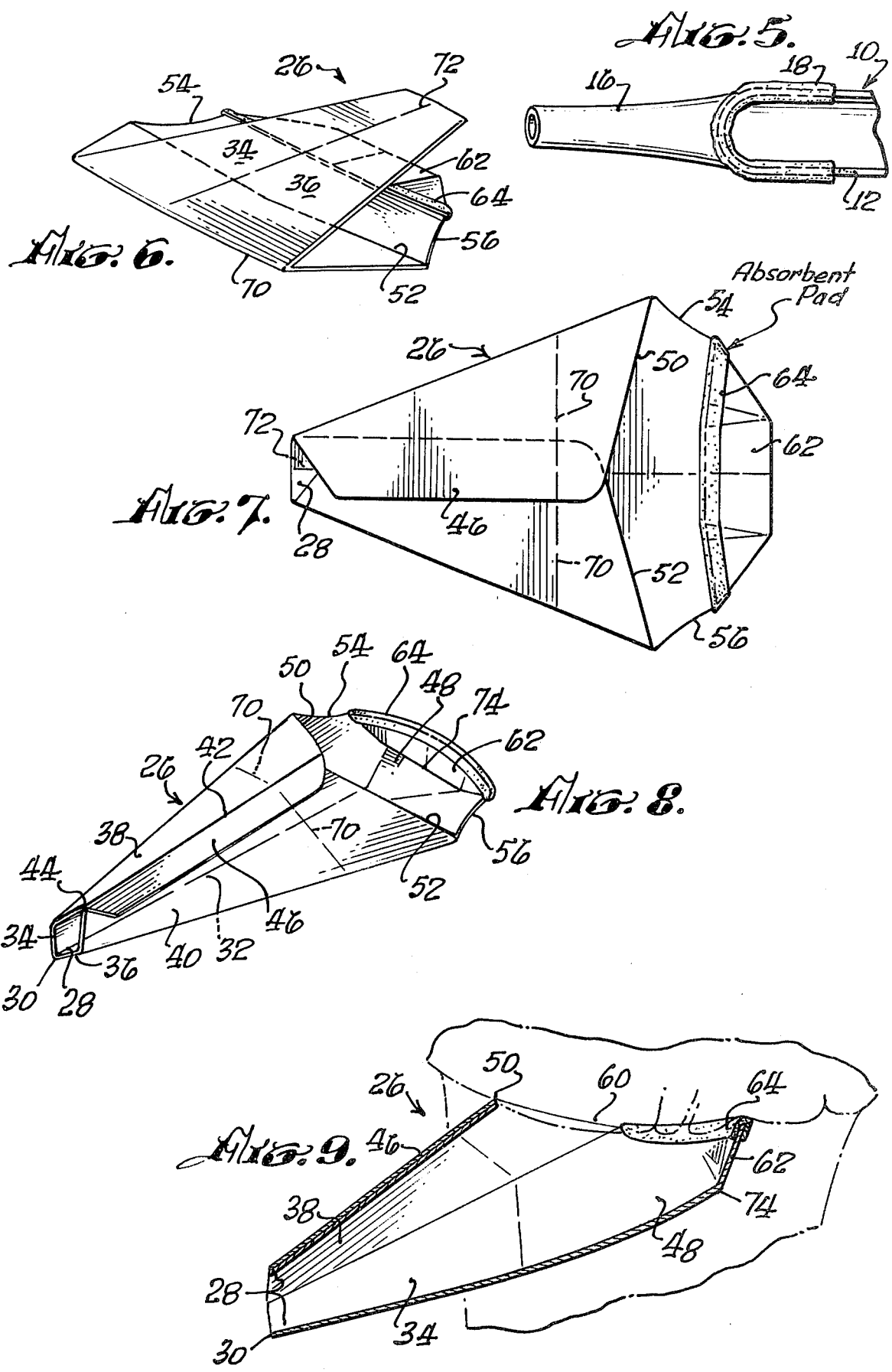

URINAL DEVICE

CROSS-REFERENCE TO RELATED APPLICATION

This application is a Continuation-in-Part of my co-pending application for a URINAL DEVICE, Ser. No. 527,887, filed Nov. 27, 1974 and now abandoned.

BACKGROUND OF THE INVENTION

1. Field of the Invention

This invention relates generally to a urinary device and relates more particularly to an improved urinal for females.

2. Description of the Prior Art

Various devices have been proposed but these are primarily for use by bed confined female patients in hospitals or the like and as far as I am aware, are not suitable for non-medical or non-hospital use by a girl or woman to urinate like a boy or man. This is especially useful where sanitary facilities are lacking.

SUMMARY OF THE INVENTION

The device may be of any suitable material such as plastic or the like and comprises a trough part which is open at the top and is adapted to be placed against the body in alignment or in register with the urethra. From the forward end of the trough, there is a discharge tube or conduit that is inclined downwardly and forwardly. There is means to remove residual urine from the internal and external vulvae by a piece of material that will absorb the urine.

The piece of absorbent material is of generally U-shaped with a channel in the underside which is U-shaped in the cross-section. The groove compliments the rear rim of the device and is adapted to snugly receive the rear rim of the trough without slippage in normal use. This material is steam and pressure molded from cut segments of continuous rope which has a high wet strength paper cover and a cotton linter core. The groove into which the rear rim of the trough fits, is lined with a thin layer of casein or gelatine based material which maintains its strength through brief exposure to moisture but dissolves upon prolonged exposures to free water thereby allowing the absorbent material to be flushed without harm to standard septic systems.

In typical use, the bicomponent device is placed against the external vulva immediately prior to urination. During urination, the stream issuing from the device is directed to a suitable spot. After urination, the device is moved forward in a smooth motion so that the rearmost portion of the device which bears the replaceable absorbent material, will blot the vulva dry, after which the absorbent material may be flicked off the device with a sharp motion which serves both to dispose of traces of urine on the device and the wetted absorbent material. The device is then either washed or stored for later washing. It is to be noted that the device is meant to be wholly external to a woman's labia.

In an alternative embodiment, the device is made of foldable liquid resistant material such as a plastic which may be unfolded into the proper shape for use. The device may also be made of waterproof paper or paper with a liquid proof lining. These devices are disposable.

OBJECTS AND ADVANTAGES OF THE INVENTION

It is an object of the invention to provide a urinal device that enables a female to urinate with minimal exposure of her person to weather (cold wind, rain, snow etc.) insects (mosquitos, black flies, chiggers etc.) and other humans;

It is still another object of the invention to provide a device of this character that enables a female to urinate without assuming unstable or dangerous positions where footing may be unsure (hilly or mountainous terrain, mud, wet grass, thorny ground etc.);

It is another object of the invention to provide a device of this character that enables a female to urinate without the embarassment and discomfort of stained clothing possible with other methods;

A further object of the invention is to provide a device of this character that enables a female to urinate in the least time, avoiding the troubles of slower methods;

A still further object of the invention is to provide a device of this character which, where sanitary facilities are poor, enables a female to avoid contact with dirty toilet seats and their associated hazards;

Another object of the invention is to provide a device of this character that enables the female to avoid painful abstention caused by inadequate sanitary facilities;

Still another object of the invention is to provide a urinal device of this character made of foldable and liquid proof material such as a suitable plastic or paper with a waterproof lining;

A further object of the invention is to provide such a foldable device having absorbent material along the rear free edge.

The characteristics and advantages of the invention are further sufficiently referred to in connection with the following detailed description of the accompanying drawings, which represent one embodiment. After considering this example, skilled persons will understand that many variations may be made without departing from the principles disclosed and I contemplate the employment of any structures, arrangements or modes of operation that are properly within the scope of the appended claims.

DESCRIPTION OF THE DRAWINGS

Referring to the drawings, which are for illustrative purposes only;

FIG. 5 is a top plan view showing the piece of absorbent material on the front free edge of the trough;

FIG. 6 is a perspective view of the foldable device in the folded condition;

FIG. 7 is a top plan view of the device in the straightened use but flat condition;

FIG. 8 is a perspective view of the foldable device in the unfolded position for use; and FIG. 9 is a longitudinal sectional view of the device in use.

DESCRIPTION OF THE PREFERRED EMBODIMENTS

Figure 1:
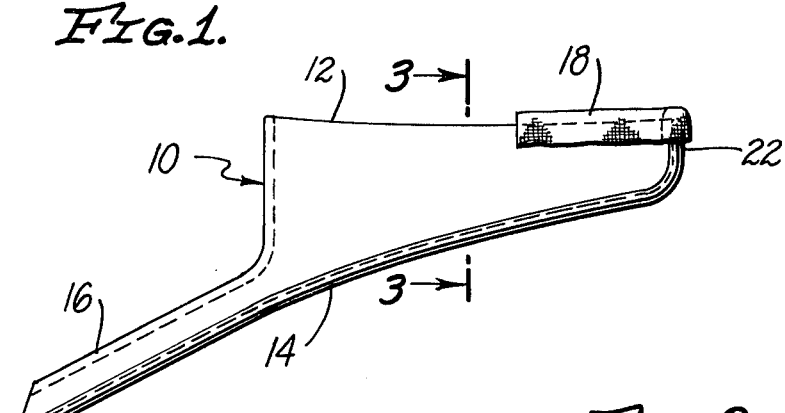
FIG. 1 is a side elevational view of a urinal device embodying the present invention.
Figure 2:
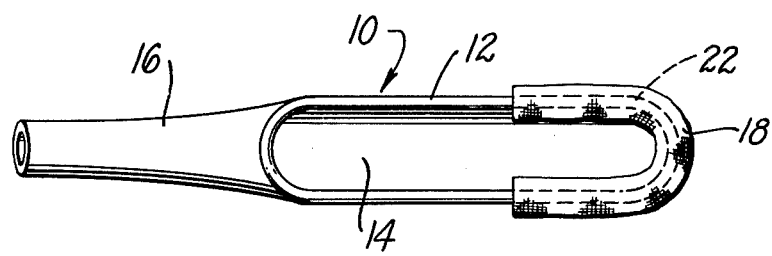
FIG. 2 is a top plan view thereof.
Figure 3:
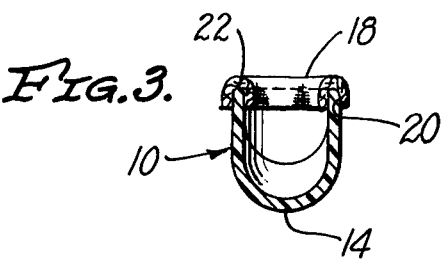
FIG. 3 is a sectional view taken on line 3—3 of FIG. 1.

Referring more particularly to FIGS. 1 through 4 of the drawings, there is shown a reusable device embodying the invention, said device comprises a trough part, indicated generally at 10 which is generally oval in shape. The trough is open at the top as at 12 and has a downwardly inclined bottom or bottom wall 14.

At the forward end of the trough, there is a discharge spout or conduit 16 which is inclined downwardly and forwardly. Said conduit communicating with the forward end and deepest part of the trough. The part just described may be of any suitable material. For example, it may be of plastic that is self shape retaining, various of such plastics being well known.

At the rear of the trough, there is a strip of liquid absorbent material 18, this piece of material is U-shaped and has a groove 20 in the underside thereof in which the rear free edge or rim of the trough is received. This absorbent material is steam and pressure molded from cut segments of a continuous strip which has a high wet strength paper covering and a cotton linter core. The absorbent material is disposed on the rear part 22 of the rim of the trough and the rim of the trough is snugly received in the groove 20 so that it will not slip under normal conditions of use. Alternatively, the absorbent material is at the forward end of the trough and on the free edge thereof as shown in FIG. 5.

The groove 20 into which the rear rim of the trough fits, is lined with a thin layer of casein or gelatine based material which maintains its strength through brief exposure to moisture but dissolves upon prolonged exposure to free water thereby allowing the absorbent material to be flushed without harm to standard septic system.

In typical use, the bicomponent device is placed against the external vulva immediately prior to urination. During urination, the stream issuing from the device is directed to a suitable spot. After urination, the device is moved forward in a smooth motion so that the rearmost portion of the device which bears the replaceable absorbent material will blot the vulva dry, after which the absorbent material may be flicked off the device with a sharp motion which serves both to dispose of traces of urine on the device and the wetted absorbent material. The device is then either washed or stored for later washing. It is to be noted that the device is maintained to be wholly external to a woman's labia.

Figure 4:
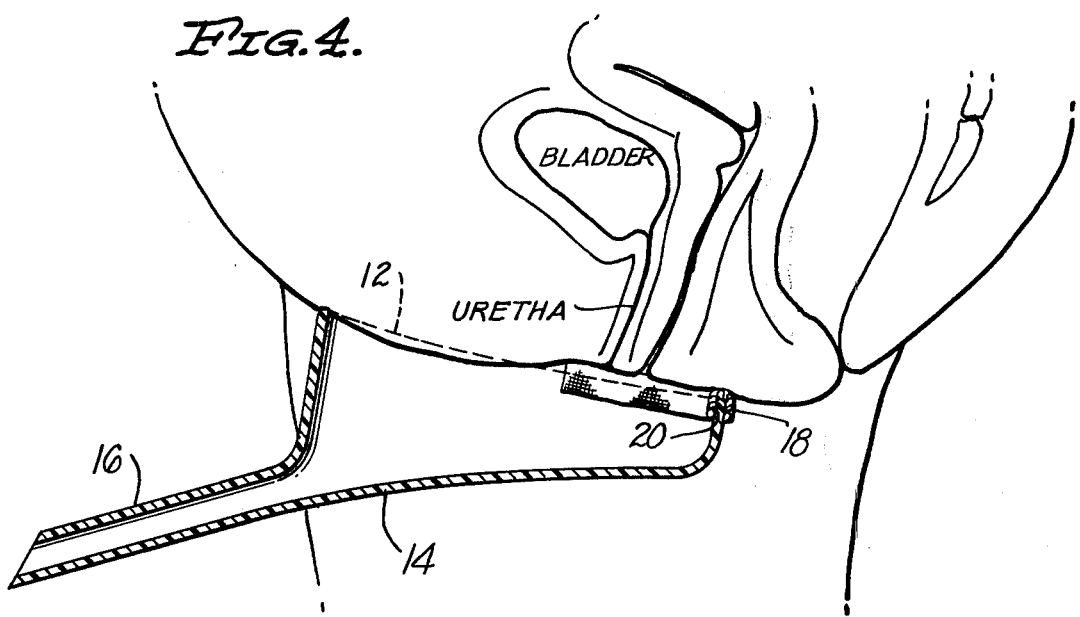
FIG. 4 is a fragmentary sectional view of the device in position for use.

Referring to FIG. 4, the device is shown in position for use. The free upper edge of the trough is disposed against the body in a position whereat it is in register with the urethra and adapted to receive the urine as it is discharged. When properly positioned, the urine will flow forwardly in the trough and be discharged through the discharge conduit or tube 16.

Referring to FIGS. 6 through 9, there is shown an alternative embodiment made of foldable material such as a liquid proof paper for example.

When in the unfolded condition, as shown in FIG. 7, the spout or conduit portion of the device is indicated generally at 26 and the discharge opening 28 is diamond-shaped with a point 30 at the bottom. From this point, there is a crease line 32 which extends rearwardly and the walls 34 and 36 at each side of the crease line define a trough, the lower edges of said walls being joined together along the crease line.

Walls 38 and 40 are turned inwardly and the free edge of wall 40 extends along a crease line 42 from the top point 44 of the diamond-shaped opening 28. Wall 38 has a longitudinally extending flap 46 which overlaps the free edge of wall 40 and is secured thereto by a suitable adhesive which is liquid resistant. The walls 34, 36, 38 and 40, define a discharge conduit or spout. The walls 34 and 36 extend rearwardly of the rear edges of the walls 38 and 40 to define a liquid collecting receptacle 48 which is upwardly opening as at 60, the opening being defined by the rear edges 50 and 52 of the side walls 38 and 40 and portions 54 and 56 of the free edges of the walls 34 and 36. At the rear, the receptacle 48 is defined by a rear end wall 62 which is an extension of rear end portions of the walls 34 and 36 and is integral with said walls. The wall 62 is inclined upwardly and rearwardly when the device is in position for use. An absorbent pad 64 is provided on the upper free edge of the rear wall 62 similarly to the pad 18 in the arrangement of FIGS. 1 through 4 and this pad is for the same purpose and function as the pad 18. Further, the absorbent pad 64 is U-shaped in cross-section and fits over the upper free edge of wall 62. Said pad being secured in a manner similar to the securing of the pad shown in the arrangement of FIGS. 1 through 5. Another means for securing the absorbent pad 64 to the device is by some suitable adhesive of any well known character.

When the device is fully folded, it is flattened and the end wall 62 turned forwardly and down onto the adjacent portion of the bottom of the receptacle of the device. The spout portion is also flattened so that the walls 38 and 40 lie on the adjacent portions of the walls 34 and 36. A forward portion of the spout is then folded rearwardly and downwardly and may overlap the folded rear wall 62.

The device has crease lines 70 and 72, being folded along the crease line 70 rearwardly and downwardly, the crease line 72 being at the bottom of the spout when the device is in the unfolded position for use and said device is folded along said crease line 72 sufficiently to cause liquid to flow downwardly and out of the spout 28. A crease line 74 is along the base of the rear wall 62 and said wall is folded forwardly and downwardly along crease line 74. In creasing the device along the crease line 72, pressure is applied at the sides of the spout sufficient to effect proper opening of the discharge outlet 28. While the absorbent pad is shown at the rear of the trough in FIGS. 6 through 9, it may be at the front end of the trough. There could, of course, be a pad at both ends but only one pad is normally required. The device is shown in use in FIG. 8 and is used in a similar manner as the device shown in FIG. 4. The device of FIGS. 6 through 9 inclusive may be disposable and may be individually packaged in an envelope or the like and dispensed in a coin operated dispensing machine. Further, a plurality of the devices may be packaged for carrying by a person intending to use same and may be removed from the package and used and, if desired disposed. While one folded arrangement is shown, it is to be understood that the foldable device may be folded in other manners.

The invention and its attendant advantages will be understood from the foregoing description and it will be apparent that various changes may be made in the form, construction and arrangement of the parts without departing from the spirit or scope thereof or sacrificing its material advantages, the arrangement hereinbefore described being merely by way of example and I do not wish to be restricted to the specific form shown or uses mentioned except as defined in the accompanying claims.

I claim:

1. A gravity-operated urinary device for use by a woman in a standing position, comprising:

means for forming an unconstrained stream of urine, and for projecting said unconstrained urine-stream through open space forwardly and away from the body of the standing woman;

said forming means comprising non-storing funneling means for gathering urine from said standing woman, and for funneling said gathered urine to a discharge conduit;

said forming means further comprising means for discharging the urine from said funneling means through open space in the form of an unconstrained urine-stream;

said funneling means comprising a funnel-like, non-storing, hollow, elongated, generally-horizontal trough defined by upright walls and open at the top, the upper edges of the walls being free, and adapted for touching-contact with the external portion of the standing woman's vulva, the opening formed by the free tops of the walls being substantially horizontal during use;

said discharging means comprising a substantially rigid discharge conduit connected to the trough at its forward end, said discharge conduit being proportioned for discharging the gathered urine as a urine-stream in the manner of a male-produced urine-stream, and for projecting the urine-stream a near-maximum distance from the standing woman.

2. The invention defined by claim 1, wherein said trough has a bottom wall sloping downwardly and forwardly, has a pair of substantially-planar and substantially-parallel side walls, and has a front wall and a rear wall—the walls defining a narrow, elongated, open-top trough adapted to be used by a standing woman;

the front wall and side walls of said trough defining a funnel-like discharge configuration proportioned to produce a substantially-unrestricted urine-flow to said discharge conduit;

and said discharge conduit is connected to the trough at its deepest end, and is inclined forwardly and downwardly so that drainage is by gravity, and is adapted to produce an unconstrained urine-stream that is directed through open space to a chosen spot.

3. The invention defined by claim 1, including moisture absorbent material attached to a portion of the trough for absorbing residual moisture after the device has been used.

4. The invention defined by claim 3, wherein there is a thin layer of material for attaching said moisture-absorbent material, said attaching material maintaining its strength through brief exposure to moisture but dissolving upon prolonged exposure to moisture.

5. A urinary device comprising:

a hollow, elongated generally horizontal trough open at the top;

a tubular conduit connected to the trough at its forward end;

said device being for use by a person in an upright position, said trough having a bottom wall sloping downwardly and forwardly, and said tubular conduit being connected to the trough at its deepest end and being inclined forwardly and downwardly;

the device is self-shape retaining material and the opening at the top of the trough is elongated;

absorbent material on the edge portion of the opening at the top of the trough and at the rear of said trough;

the absorbent material being elongated and U-shaped with a groove in the underside, said groove being generally U-shaped in cross-section and removably attachable to the rear rim portion of the trough; and wherein the groove of the absorbent material is lined with a thin layer of casein or gelatine based material which maintains its strength through brief exposure to moisture but dissolves upon prolonged exposure to moisture.

6. The invention defined by claim 2, wherein the device is of foldable material at least temporarily impervious to liquid.

7. The invention defined by claim 6, wherein the device when in a folded condition, has the top flattened onto the bottom with a top portion and a back wall portion folded forwardly onto the adjacent flattened portion, and the conduit portion being folded rearwardly and downwardly, there being crease lines for folding the conduit portion into the flattened position and the back portion folded forwardly and downwardly, there also being a crease line for the bottom of the conduit and extending longitudinally thereof.

8. The invention defined by claim 6, wherein the top has a pair of walls, a tab on the free edge of one of said walls and overlapping the other wall and sealed thereto and comprises means for securing the device together.

* * * * *